United States Patent [19]
Lodi et al.

[11] Patent Number: 6,020,359
[45] Date of Patent: *Feb. 1, 2000

[54] PHARMACEUTICAL COMPOSITION

[75] Inventors: Andrea Lodi; Maria Teresa Rossato, both of Verona, Italy

[73] Assignee: Glaxo Wellcome SpA, Verona, Italy

[*] Notice: This patent is subject to a terminal disclaimer.

[21] Appl. No.: 09/228,931

[22] Filed: Jan. 12, 1999

Related U.S. Application Data

[62] Division of application No. 08/875,114, Jul. 25, 1997, Pat. No. 5,886,018.

[30] Foreign Application Priority Data

Feb. 11, 1995 [GB] United Kingdom .................. 9502695

[51] Int. Cl.$^7$ ................................................ A61K 31/405
[52] U.S. Cl. ............................................................. 514/419
[58] Field of Search ............................................. 514/419

[56] References Cited

U.S. PATENT DOCUMENTS 5,106,847   4/1992   Salituro et al. ...................... 514/232.5
5,886,018   3/1999   Lodi et al. .............................. 514/419

FOREIGN PATENT DOCUMENTS 0 396 124   11/1990   European Pat. Off. .
0 568 136   11/1993   European Pat. Off. .

OTHER PUBLICATIONS

Remington's Pharmaceutical Sciences (15th ed.) 1975, p. 759.

*Primary Examiner*—Phyllis G. Spivack
*Attorney, Agent, or Firm*—Bacon & Thomas

[57] ABSTRACT

A Pharmaceutical composition in a form suitable for parenteral administration comprising a solution of the glycine antagonist (E)-3-[2-phenylcarbamoyl) ethenyl]-4,6-dichloroindole-2-carboxylic, acid or a physiologically acceptable salt thereof, in an isotonic sugar solution containing a water miscible organic solvent for the compound, said formulation having a pH within the range of 7 to 9.

6 Claims, No Drawings

PHARMACEUTICAL COMPOSITION

This application is a Divisional of U.S. application Ser. No. 08/875,114 filed Jul. 25, 1997, now U.S. Pat. No. 5,886,018.

This invention relates to pharmaceutical composition for parenteral administration. More particularly it relates to aqueous formulations of a glycine antagonist for parenteral administration.

UK Patent Application GB 2266091A describes (E)3[2-(phenylcarbamoyl)ethenyl])-4,6-dichloroindole-2 caboxylic acid and physiologically acceptable salts or metabolically labile esters thereof which exhibit antagonist activity at the strychnine insensitive glycine binding site associated with the NMDA receptor complex. Further, the specification teaches that the compound may be formulated for parenteral administration and, in particular, an aqueous solution for injection R consisting of the active ingredient, sodium phosphate, water for injection and sufficient sodium hydroxide to adjust to the pH or the solution to within the range 3–10.

We have now surprisingly found that an improved formulation for parenteral administration may be obtained if the glydne antagonist is formulated in an isotonic sugar solution suitable for injection containing a water miscible organic solvent for the compound and the pH of the solution is adjusted to be within the range 7 to 9.

Thus the present invention provides a pharmaceutical composition in a form suitable for parenteral administration comprising a solution of E-(3)-[2-(phenylcarbamoyl) ethenyly]-4,6-dichloroindole-2-carboxyric acid, or a physiologically acceptable salt thereof, in an isotonic sugar solution containing a water miscible organic solvent for the compound, said composition having a pH within the range 7 to 9.

The isotonic sugar solution for use in the composition is conveniently an aqueous dextrose solution such as 2 to 5% dextrose solution. Examples of suitable alternative isotonic sugar solutions include those containing mannitol or sorbitol.

Conveniently the composition according to the invention is prepared from the glycine antagonist E-3-[2-(phenylcarbamoyl)ethenyl]-4,6-dichloroindole-2-carboxylic acid in the form of the free acid or more particularly in the form of the sodium salt thereof.

The amount of the glycine antagonist (expressed in terms of the free acid) in the formulation is preferably within the range 0.1 to 80 mg/ml.

If necessary, the pH of the solution may be adjusted by the addition of a suitable base such as aqueous sodium hydroxide. More conveniently however, the pH of the solution may be adjusted to and/or maintained within the range 7 to 9, e.g, 8.0 to 9.0 by the use of a suitable buffer salt Examples of suitable buffer salts include tris (hydroxymethyl) aminomethane or alkali metal salts of citric acid and or phosphoric acid, e.g., disodium phosphate. A particularly convenient buffer salt for use in the invention is tris(hydroxymethyl) aminomethane.

Suitable water miscible organic solvents for use in the formulation include propylene glycol, glycofurol, ethanol, benzyl alcohol, glycerol, polyethylene glycols, N-methyl pyrrolidone or dimethylacetamide. The amount of water miscible organic solvent present is conveniently within the range of 0.1 to 40% by weight of the total formulation.

The formulation accorrding to the invention may be administered in the form of a bolus injection or intravenous infusion. For the bolus injection the amount of water miscible organic solvent present is conveniently within the range 5 to 40% and the concentration of the glydne antagonist is conveniently within the range of 10 to 80 mg/ml e.g. 20–70 mg/ml. A particularly convenient water miscible organic solvent for use in the bolus injection is glycofurol. The isotonic sugar solution for use in the bolus injection is conveniently an aqueous mannitol solution.

For the intravenous infusion the amount of water miscible organic solvent is conveniently within the range 1 to 4% and the concentration of the glycine antagonist is conveniently in the range of 0.1 to 5 mg/ml e.g. 0.5 to 2 mg/ml. A particularly convenient water miscible organic solvent for use in intravenous infusion is propylene glycol. A particularly useful sugar for use in the intravenous infusion formulation is dextrose.

For the intravenous infusion formulation and more particularly those wherein the concentration of glycine antagonists (expressed as the free acid) is higher than 0.8 mg/ml, the solubility of the glycine antagonist in the infusion solution may be improved or enhanced by the addition of ethylene diamine tetraacetic acid (EDTA) and/or physiologically acceptable salts thereof. Examples of suitable salts of EDTA include ammonium salts such as the diamrionium salt or alkali metal salts as such the di, tri or tetra sodium or potassium salts thereof. A particularly convenient salt is the disodium salt, e.g., EDTA disodium salt dihydrate. The minimum amount of EDTA or a salt thereof required to ensure good solubility will depend upon a number of factors including the choice of water miscible organic solvent and or the sugar present, however, actual minimum amount required for a given formulation may be readily determined by simple experimentation. As a general rule, however, the minimum amount of EDTA or a salt thereof required (expressed as free acid) will be in the region of 0.3% of the amount of glycine antagonist (expressed as a free acid) present. It will be appreciated that the amount of EDTA or a salt thereof present in the formulation may be more than the minimum required to achieve the desired level of solubility of the glycine antagonist in the formulation.

The composition according to the invention, and more particularly the composition for administration as a bolus injection, may also contain a surfactant. Examples of suitable surfactants include polysorbates, e.g., polysorbate 80.

Conveniently, the formulation according to the invention may be prepared by dissolving the glycine antagonist in the water miscible organic solvent or an aqueous mixture thereof. Also if required, the buffer salt and or the EDTA or a salt thereof may be added at this time. When desired, the resultant solution is then mixed with the isotonic sugar solution.

The following examples illustrate the invention. In these examples the glycine antagonist is used in the form of its sodium salt.

Example A

| | Amount per ml |
|---|---|
| Glycine antagonist | 1.69 mg |
| Tris (hydroxymethyl)aminomethane | 0.72 mg |
| EDTA disodium salt dihydrate | 0.00768 mg |
| Water | 3.192 mg |
| Propylene glycol | 0.0194 ml |
| Dextrose solution 5% w/v | qs t0 1 ml |

The tris(hydroxymedthyl)aminomethane and the EDTA disodium salt dihydrate were dissolved in water; the propylene glycol was added and the glycine antagonist was dissolved therein. The solution was filtered through a sterile 0.2 micron sterilizing filter and filled in a container that was finally sterilized by autoclaving.

The solution was then diluted with the 5% dextrose solution suitable for injection.

| Example B | |
|---|---|
| | Amount per ml |
| Glycine antagonist | 0.83 mg |
| Tris(hydroxymethyl)aminomethane | 0.36 |
| Water | 1.596 |
| Propylene glycol | 0.0097 ml |
| Dextrose solution 5% | qs to 1 ml |

Example B was prepared using the same procedure as described for example A except that the EDTA disodium salt dihydrate was omitted.

| Example C | |
|---|---|
| | Amount per ml |
| Glycine antagonist | 0.83 |
| Disodium phosphate | 0.7 mg |
| Propylene glycol | 0.016 ml |
| Dextrose solution 5% w/v | qs to 1 ml |

The glycine antagonist was dissolved in the propylene glycol, the solution filtered through a sterile 0.2 micron sterilizing filter. The solution was then mixed with the 5% dextrose solution suitable for injection containing the disodium phosphate. Conveniently, the mixing may be carried out in a container for infusion.

| Bolus Injection | |
|---|---|
| | Amount per ml |
| Glycine antagonist | 70.6 mg |
| Polysorbate 80 | 10 mg |
| Tris(hydroxymethyl)aminomethane | 1.3 mg |
| Glycofurol | 300 mg |
| 5% Aqueous Mannitol | qs to 1 ml |

A solution of tris(hydroxymethyl)aminomethane in the 5% aqueous mannitol is added portionwise to a solution of the gylcine antagonist in a mixture of the polysorbate 80 and glycofurol. The resulting solution is filtered through a sterile 0.2 micron sterilizing filter, filled into containers and then sterilized by autoclaving.

We claim:

1. A composition comprising a solution of (E)-3-[2-(phenylcarbamoyl) ethenyl]-4,6-dichloroindole-2-carboxylic acid or a physiologically acceptable salt thereof in a water miscible organic solvent or an aqueous mixture thereof, optionally containing a buffer salt and/or ethylene diamine tetra acetic acid or a physiologically acceptable salt thereof, suitable for mixing with an isotonic sugar solution to provide a pharmaceutical composition in a form suitable for parenteral administration comprising a solution of a glycine antagonist which is (E)-3-[2-(phenylcarbamoyl) ethenyl]-4,6-dichloroindole- 2-carboxylic acid or a physiologically acceptable salt thereof, in an isotonic sugar solution containing a water miscible organic solvent for the compound, said formulation having a pH within the range of 7 to 9.

2. A composition as claimed in claim 1 containing a buffer salt.

3. A composition as claimed in claim 2 wherein the buffer salt is (tris hydroxymethyl) aminomethane.

4. A pharmaceutical composition as claimed in claim 3 wherein the composition is prepared using the sodium salt of (E)-3-[2-(phenylcarbamoyl)ethenyl]-4,6-dichloroindole 2-carboxylic acid.

5. A pharmaceutical composition as claimed in claim 2 wherein the composition is prepared using the sodium salt of (E)-3-[2-(phenylcarbamoyl)ethenyl]-4,6-dichloroindole 2-carboxylic acid.

6. A pharmaceutical composition as claimed in claim 1 wherein the composition is prepared using the sodium salt of (E)-3-[2-(phenylcarbamoyl)ethenyl]-4,6-dichloroindole 2-carboxylic acid.

* * * * *